United States Patent [19]

Di Giovanni

[11] Patent Number: 4,591,085
[45] Date of Patent: May 27, 1986

[54] SURGICAL INSTRUMENT FOR APPLYING FASTENERS, SAID INSTRUMENT HAVING AN IMPROVED TRIGGER INTERLOCKING MECHANISM (CASE VI)

[75] Inventor: John Di Giovanni, Woodbridge, N.J.

[73] Assignee: Ethicon, Inc., Somerville, N.J.

[21] Appl. No.: 631,116

[22] Filed: Jul. 16, 1984

[51] Int. Cl.⁴ ............................................. A61H 17/00
[52] U.S. Cl. .................................. 227/8; 128/334 R; 227/19; 227/DIG. 7
[58] Field of Search ....... 128/334 R; 227/19, DIG. 7, 227/83, 8

[56] References Cited

U.S. PATENT DOCUMENTS 4,207,898  6/1980  Becht ................................. 128/305
4,351,466  9/1982  Noiles ................................. 227/8

FOREIGN PATENT DOCUMENTS

2141066  12/1984  United Kingdom ............ 128/334 R

Primary Examiner—Paul A. Bell
Attorney, Agent, or Firm—Robert L. Minier

[57] ABSTRACT

A surgical instrument for stitching tissue having a stationary grip portion and a movable trigger portion which are interlocked until the jaws of the instrument are in proper position for stitching tissue.

3 Claims, 12 Drawing Figures

SURGICAL INSTRUMENT FOR APPLYING FASTENERS, SAID INSTRUMENT HAVING AN IMPROVED TRIGGER INTERLOCKING MECHANISM (CASE VI)

This invention relates to medical instruments and more particularly to instruments for joining tissue organs by using fasteners. Preferably the fasteners are two piece with one part of the fastener is a U-shaped staple and the other part of the fastener a receiver which interlocks with the legs of the staple to form the fastener.

BACKGROUND OF THE INVENTION

Over the years various surgical instruments for joining tissue have been developed. Most instruments have been developed utilizing metal staples for joining the tissue. The metal staples are relatively rigid, have their legs sharpened to readily penetrate the tissue, and once penetrated may then be crimped into a clinched position to hold the tissue together as is well known in the art. Instruments of this type are more fully disclosed and described in U.S. Pat. Nos. 3,080,564, 3,079,606, 2,891,250, 3,589,589, 4,207,898 and 4,351,466.

Generally, the instruments comprise a movable member or jaw and a stationary member or jaw. The movable jaw usually carries the metal staples and the stationary jaw carries an anvil which clinches or bends the legs of the staple that pass through the tissue. In use, the tissue is placed between the jaws, the jaws brought to the appropriate gap and the staples driven through the tissue and clinched to set the staple. A major problem with these instruments is the use of the metal staple. While metal staples provide desired hemostatsis in the joining of the tissue, they remain in the tissue and can disrupt future diagnostic techniques such as x-ray diagnosis, computer axial tomography, nuclear magnetic resonance, and the like. To eliminate this problem, it has been found desirable to develop instruments which can set nonmetallic fasteners. These are fasteners made from biologically absorbable or non-absorbable polymeric materials. Examples of such non-absorbable polymeric materials would be the polyolefins, polyesters, and the like. Examples of the absorbable polymeric materials would be the polymers and copolymers of glycolide, lactide, dioxanone, etc. These polymeric materials do not have the dead-bend morphology of a metal and, hence, they cannot be clinched in the same manner as a metal staple. To use these polymers, the fasteners are designed as two-piece fasteners. This means one piece of the fastener is placed on one side of the tissue to be joined and the second piece of the fastener is placed on the other side of the tissue to be joined. One piece of the fastener is a U-shaped staple which has legs which are caused to penetrate the tissue. On the opposite side of the tissue is the second fastener piece or receiver which is a member used to engage the legs to interlock therewith once the legs have penetrated the tissue and, hence, join the tissue together.

As can be appreciated this major change in design and configuration of fasteners causes a number of problems. First, the fasteners must be designed to be sufficiently sharp and strong to penetrate the tissue or in certain instances some aiding means must be used with the fastener to assist in penetrating the tissue. Also, the fasteners must be designed to develop an interlocking between the two pieces.

These differences cause various types of forces to be used when joining the tissue together, and these forces are different from the forces required when joining tissue using metallic fasteners. Also, when utlizing the two-piece fasteners, alignment between the two fasteners is extremely critical. As can be appreciated, when applying these fasteners the instrument must hold the pieces until one piece has penetrated the tissue and the opposite piece is interengaged and locked on to the penetrating portion of the other member. Once this is accomplished the instrument must then release both pieces preferably simultaneously.

Surgical instruments whether reusable or disposable and whether they apply a metal or a plastic fastener should be extremely reliable. They should function with absolute certainty and each instrument should function in the same manner. Such repetitive reliability is required to allow surgeons to adequately develop their surgical techniques and to keep trauma to a minimum during surgical procedures. Along with this desirable total repetitive reliability the instrument should be simple to construct and economical to produce. In surgical instruments for placing fasteners it is important that the instrument not be actuatable to place the fastener until the tissue is in place to be joined and the appropriate gap has been set between the jaws of the instrument.

It is an object of the present invention to provide instruments having identical actions and operations especially in the placement of the fastener once the appropriate gap has been set between the jaws of the instrument. It is also an object of the present invention to provide an instrument which is simple in construction and economical to produce.

SUMMARY OF THE PRESENT INVENTION

The present invention provides a surgical instrument for joining tissue by means of staples or other fasteners. The fasteners may comprise a U-shaped staple member with or without a receiver for engaging with the legs of said staple member. The instrument places the staple member on one side of the tissue to be joined and the receiver, if one is used, on the opposite side of the tissue. The instrument causes the staple legs to penetrate the tissue and engage and interlock with the receiver or it may merely crimp the staple legs when no receiver is used. The instrument comprises a support body. Mounted at one end of the support body is a pair of jaws. A staple housing is mounted in one of the jaws and this jaw is movable with respect to the other of said jaws. Means are mounted in the support body for moving the jaw housing the staples towards the stationary jaw to close the gap between the jaws and clasp the tissue therebetween. Drive means are mounted on the support body for driving the staples from the jaw in which the staple housing is mounted towards the opposite jaw. Actuating means are mounted at the end of the support body opposite the end at which the jaws are mounted for actuating the staple drive means. In preferred embodiment of the instrument of the present invention, there is means cooperating with the open end of the jaws to hold tissue in place between the jaws while the staples are being driven.

The instrument includes interlocking means to prevent the actuating means from being actuated until an appropriate gap has been set between the jaws of the instrument. The interlocking means is preferable a single pivotal member which moves out of the way of the actuating means to allow the actuating means to be actuated. In the preferred embodiment the pivotal member automatically pivots out of the way of the actuating means when an appropriate gap has been set between the jaws. Other features and details of the present invention will be discussed in the ensuing detailed description and drawings.

DETAILED DESCRIPTION OF THE DRAWINGS

Figures 1, 2, 3:
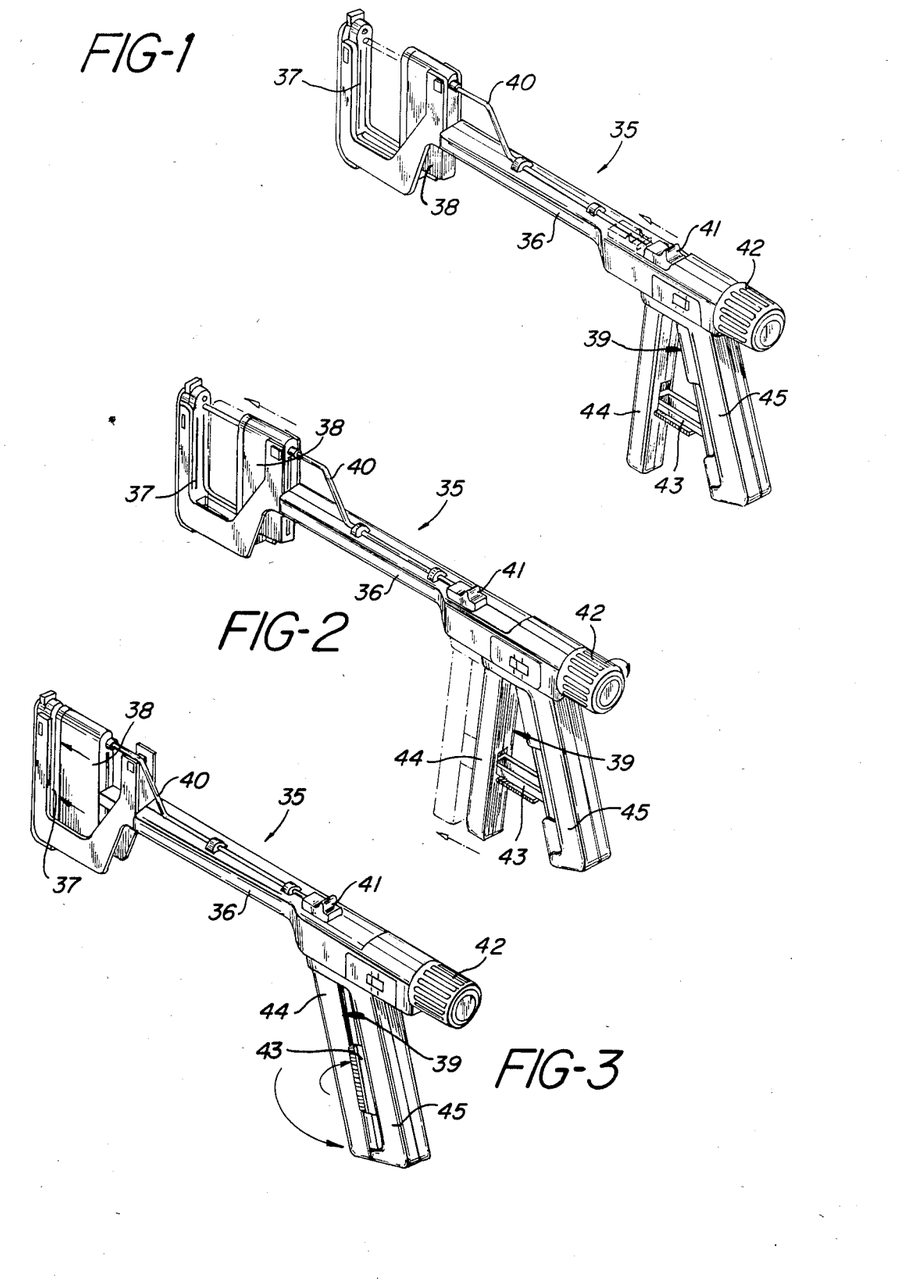
FIG. 1 is a perspective view of an instrument according to the present invention in its fully opened position.
FIG. 2 is a perspective view of the instrument of FIG. 1 in a partially open position.
FIG. 3 is a perspective view of the instrument of FIG. 1 in its firing position.

Referring to the drawings, in FIGS. 1, 2 and 3 there is depicted a surgical instrument 35 of the present invention useful for joining tissue. The instrument is depicted in three different positions.

In FIG. 1, the instrument is shown in the fully open position. The instrument comprises a support body, 36. A pair of jaws 37 and 38 are positioned at one end of the support body. Mounted at the opposite end of the support body is means 39 for actuating the instrument. In FIG. 1, the jaws of the instrument are in the open position ready to be placed about the tissue to be joined.

In FIG. 2, the jaws have been moved closer to one another to produce an appropriate gap to clamp tissue in position between the jaws so that the tissue is ready to be stitched together.

FIG. 3 shows the instrument after it has been actuated and the tissue has been joined by the instrument.

One of the jaws 37 is stationarily mounted at one end of the support body 36. This jaw carries a plurality of receivers of the two-part fastening members used with the instruments of the present invention. The opposite jaw 38, carries the U-shaped fastening members, and is movably mounted on the support body. The tissue to be joined is placed between the two jaws and the movable jaw positioned with respect to the stationary jaw at an appropriate gap. Once the tissue is placed between the jaws, the locking arm 40 is moved forwardly by the pusher 41 to insure that the tissue is held between the jaws. Once the arm is set and engaged by the stationary jaw, the knob 42 at the opposite end of the support body is turned to move the movable jaw towards the stationary jaw and set the appropriate gap between the jaws. Once the gap has been appropriately set, the trigger locking lever 43 may be disengaged and the movable portion 44 of the actuating trigger means moved towards the stationary portion 45 of the trigger means to cause an appropriate pusher to drive the staples forward causing the legs of the staples to penetrate the tissue between the jaws and the legs of the staples to enter the appropriate receivers held in the stationary jaw. Once this is accomplished the knob 42 may be turned in the opposite direction to open the jaws, the locking lever pushed back and the joined tissue separated from the jaws of the instrument.

Figure 4:
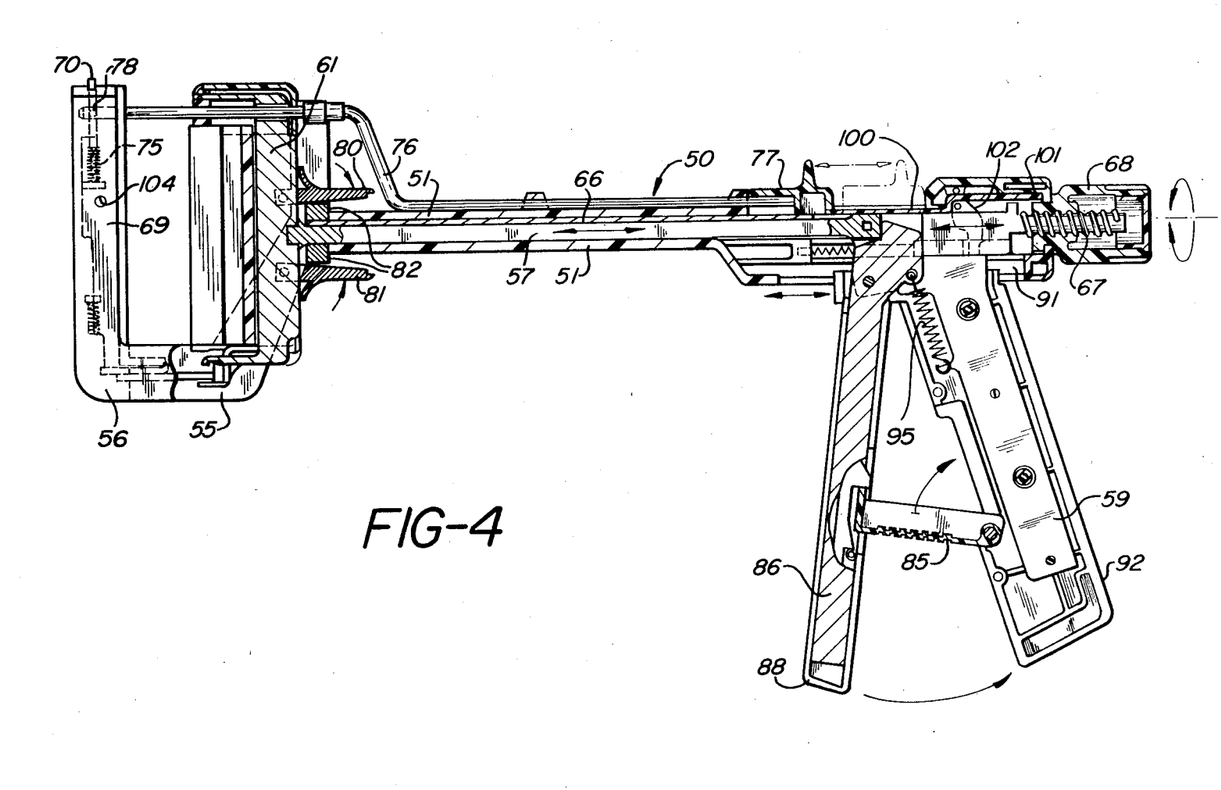
FIG. 4 is a cross-sectional another embodiment of a surgical instrument according to the present invention.
Figure 5:
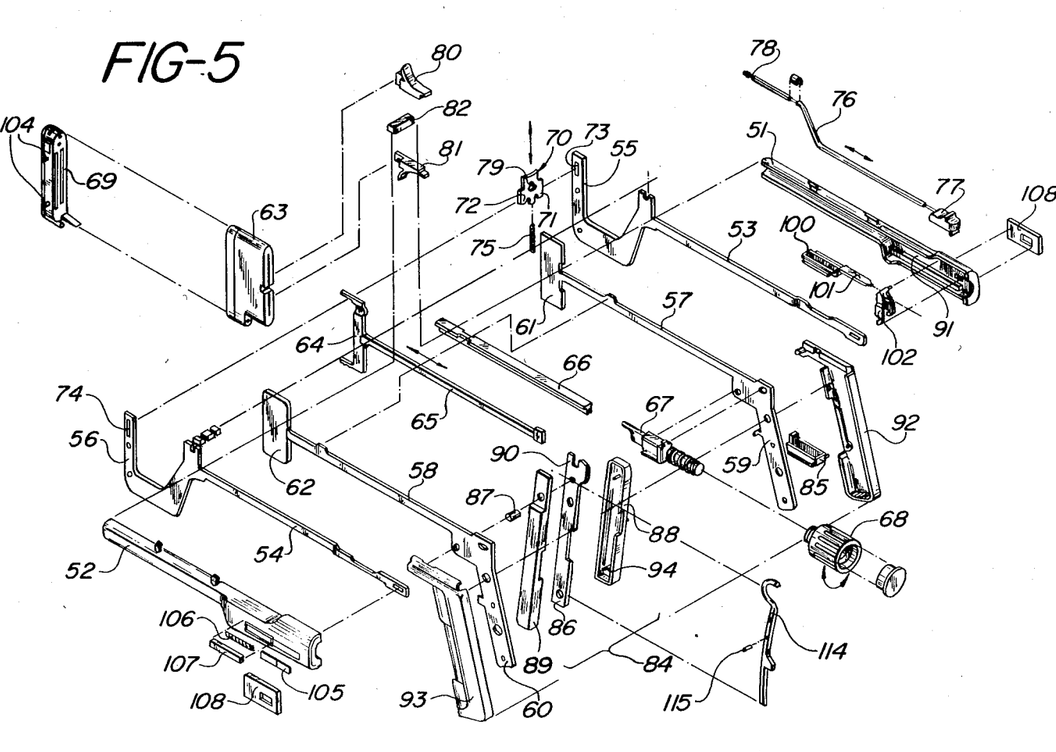
FIG. 5 is an exploded perspective view of the surgical instrument of FIG. 4.

FIG. 4 is a cross-sectional view of one embodiment of a surgical instrument according to the present invention and FIG. 5 is an exploded perspective view showing the different parts of the surgical instrument shown in FIG. 4. The body 50 of the instrument comprises a pair of outer cover members 51 and 52 which when pressed together form a hollow opening longitudinally disposed therebetween. Mounted in this opening are a pair of shafts 53 and 54 which, at one end, carry stationary supports 55 and 56 which together form the stationary jaw. The jaw is held together by riveted pins 104 located in holder 69. Also carried in the opening is a second pair of shafts 57 and 58 which carry at one end the supports 59 and 60 for the stationary portion of the actuating means and at the opposite end carry the supports 61 and 62 for the movable jaw. A holder 69 for the receivers portions of the fasteners is mounted between the stationary jaw supports and the holder 63 for the U-shaped staple portion of the fasteners is mounted between the movable jaw supports 61 and 62. A pusher 64 is mounted on a shaft 65 disposed in the center of the opening formed by the outer cover members. Mounted on top of the center shaft 65 is a movable member 66. The movable member is appropriately mounted through a screw 67 to the knob 68. Turning of the knob in one direction moves the pusher and the staple holder forwardly towards the receiver holder to set an appropriate gap between the staples and the receivers. Turning the knob in the opposite direction moves the pusher and staple holder away from the receiver holder to open the gap and allow tissue to be removed from between the staple holder and receiver holders.

Mounted between the supporting jaw members at the top thereof is a portion of means for holding tissue between the jaws and for locking the top of the jaws together to provide rigidity. This portion comprises a movable slotted member 70 having a pair of ears 71 and 72. The ears are disposed in slots 73 and 74 disposed in stationary supports 55 and 56. A compression spring 75 is mounted beneath the slotted member to allow the member to move up and down in the slots disposed in the stationary jaw members. Mounted on top of the outer cover members 51 and 52 and longitudinally thereto is the cooperating portion of the means for holding tissue and locking the jaws together for rigidity. This cooperating portion is a longitudinal movable member 76 that fits through an opening in the upper portion staple holder member 63. The longitudinally movable member is movable forwards and backwards with respect to the outer cover and is moved by the thumbs press 77. The movable member has a slot 78 at its free end and when moved forwardly, interlocks with the opening 58 in the movable slot member 70. A tab depends from the thumb press and fits into grooved member 100 mounted at the back and on top of the cover members. At the opposite end of the groove is a portion 101 that extends inwardly and engages in a slot in the knob 68. The portion 101 is guided in its movement by outer covers 51 and 52. Until the member is pushed as far forwardly as possible to remove the portion 101 from the slot in the knob, the knob cannot be rotated. Mounted from the staple holder are a pair of pawls 80 and 81 and mounted on the rigid shifts 53 and 54 is an anchor 82. The pawls are so disposed as to interlock with the anchor when the appropriate gap is set between the staple holding member 63 and the receiving holding member 69. The interlocking pawls and anchor provide added rigidity to the instrument and allow greater forces to be used when driving the staples through the tissue and into locking relationship with the receivers. At the opposite end of the instrument is mounted the trigger or actuating means 84. The actuating means comprises a trigger member 86 pivotally mounted between the supports 57 and 58 by a pin 87. The trigger member includes a pivoted interlocking member 90. The actuating means 84, members 61 and 62 and the shaft 65 are slideably mounted in slot 91 in the outer cover members 51 and 52. The stationary trigger supports are encased by a pair of plastic handle halves 92 and 93. Mounted between the movable trigger and the stationary trigger supports 59 and 60 is a second pivotal interlocking member 85. This member is pivotally mounted between the stationary handles 92 and 93 and interlocks by engaging clog 95 on the first pivoted interlocking member 90. Mounted in the cover member 52 is a gauge to tell when the correct gap is attained between the receiver holder and the staple holder. The gauge comprises a marked member 105 that is linked to the screw member 67 and is mounted in position on the cover member 52 by a spring 106 and cover plate 107. Appropriate cover plate 108 is for identification and to see the mark on the marked member are placed on the outside of the cover members.

Figure 6:
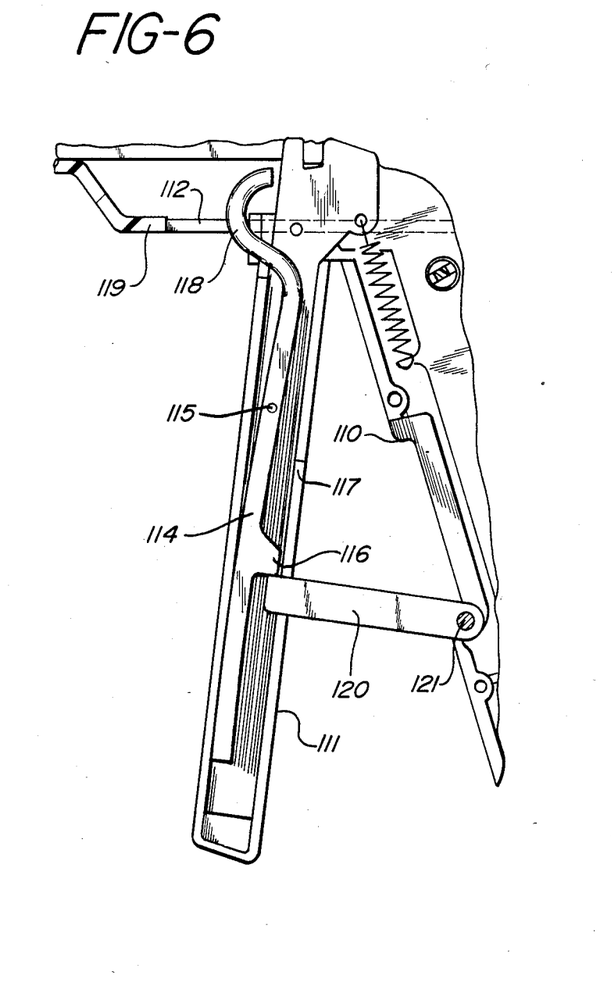
FIG. 6 is an enlarged cross-sectional view of one type of interlocking mechanism for the actuating means in a locked position.
Figure 7:
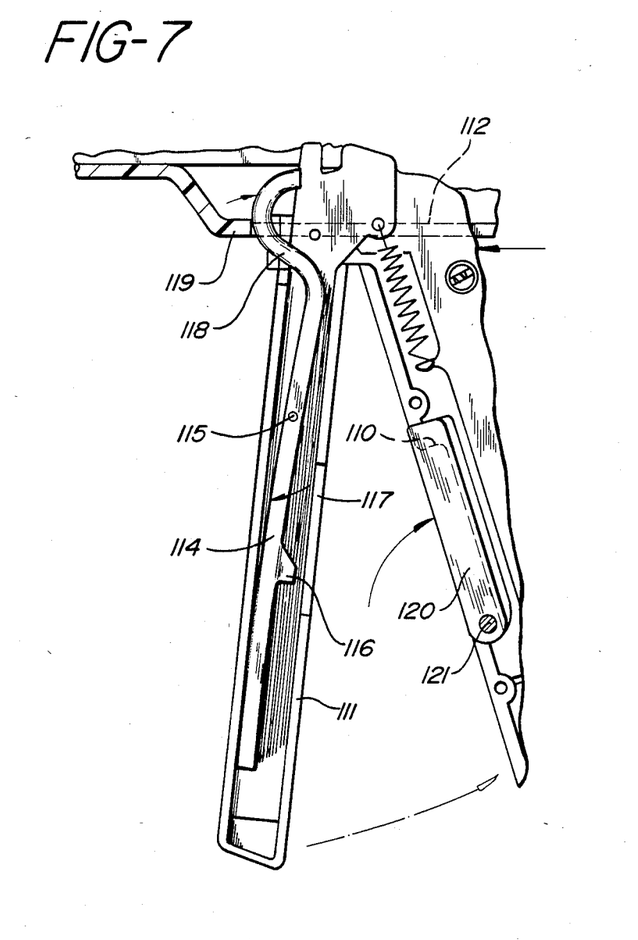
FIG. 7 is an enlarged cross-sectional view of the mechanism of FIG. 6 in the unlocked position.

FIG. 6 and 7 are enlarged cross-sectional views of the trigger mechanism of the present invention and the interlocking means which prevent actuation of the trigger unless and until the appropriate gap has been set between the jaws of the instrument. FIG. 6 shows the trigger mechanism in its locked position and FIG. 7 shows the trigger mechanism in the unlocked position. The trigger mechanism comprises a stationary grip portion 110 and a movable trigger portion 111. The stationary grip portion depends from the shaft 112 carrying the movable jaw of the instrument. The movable trigger portion is pivotally mounted by pin 113 from the movable jaw shaft 112. Appropriate stages (not shown for the sake of clarity), prevent the movable trigger portion from opening too far. The movable trigger portion is connected to the staple driving means by appropriate linkage (also not shown for the sake of clarity), so that when the movable trigger portion is squeezed and urged towards the stationary grip portion the staples are fired and driven through the tissue. The movable portion of the trigger is hollow and mounted in the hollow portion is a first pivotal lever 114. The first pivotal lever is mounted on a pin 115 extending from the movable trigger portion. The first pivotal lever also includes a clog 116 which extends out of the movable trigger portion through an opening 117. Extending from the pin in a direction opposite to the clog 116 is a hooked end 118 of the first pivotal lever. In operation as an appropriate gap is set between the jaws of the instrument and the trigger mechanism moves forward, with respect to the support shaft, the hook portion engages an ear 119 on the shaft pivoting the lever 114 and causing the clog 116 to move into the opening in the movable trigger portion. A second pivotal lever 120 is mounted by a pin 121 on the stationary grip portion. Before the gap between the jaws is set the second pivotal lever is placed in a substantially horizontal position as shown in FIG. 6 and held in the position by the clog 116 to lock the trigger mechanism in place and prevent the staples from being fired. As seen in FIG. 7, when the appropriate gap between the jaws is set the clog 116 enters the movable trigger portion and the second pivotal lever may be rotated out of the way to allow the movable trigger to be squeezed and urged towards the stationary grip thus firing the staples.

Figure 8:
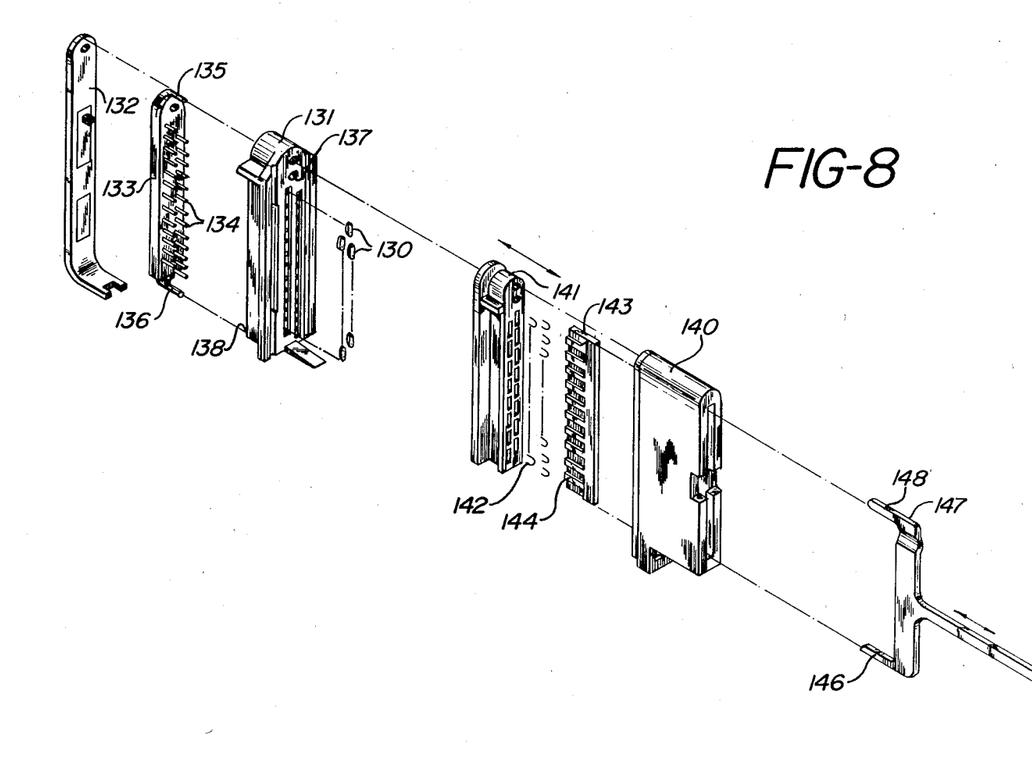
FIG. 8 is an exploded perspective view of the working parts of one embodiment of the jaws of the instrument of the present invention.
Figure 9:
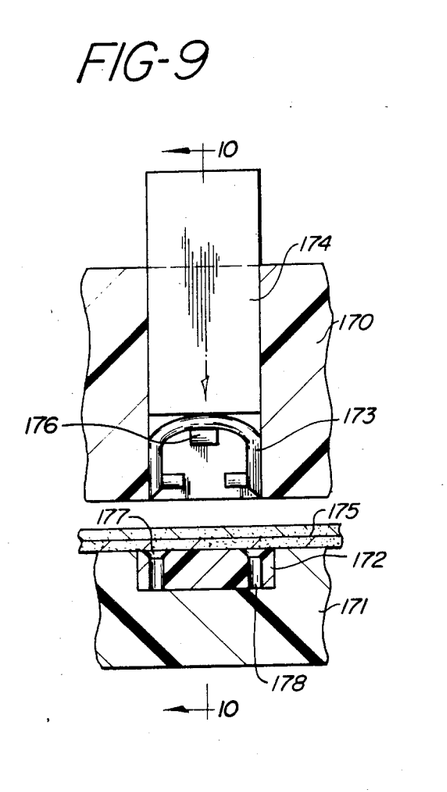
FIG. 9 is an enlarged cross-sectional view of a staple and receiver in the jaws of an instrument of the present invention.
Figure 10:
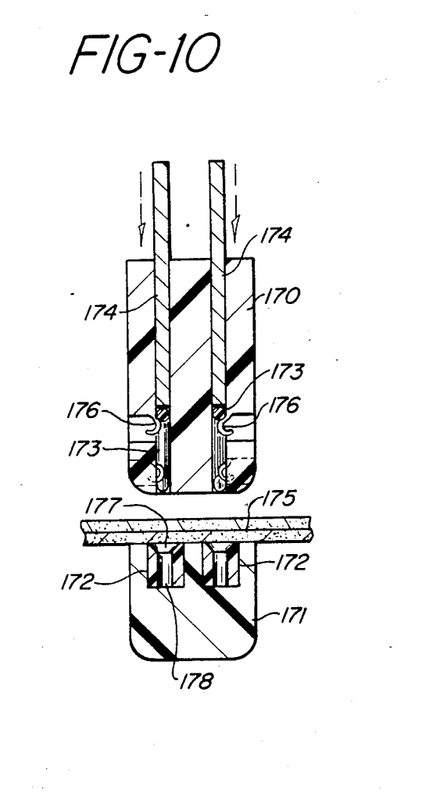
FIG. 10 is a cross-sectional view taken along line 10-20 of FIG. 9.

Referring to FIG. 8 there is shown an exploded perspective view of one embodiment of the working parts of the pair of jaws of instruments according to the present invention. Receivers, and in this instance they comprise members having a pair of openings disposed therein, are mounted in a stationary jaw and U-shaped staples with the legs of the U designed to enter the openings of the receivers are mounted in the movable jaw. The receivers 130 are mounted in a housing 131 mounted on the stationary jaw 132. The receivers are held in that housing by a movable member 133 which has pins 134 which frictionally engage the openings in the receivers. This holding member is movably mounted by virtue of an upper and a lower pin 135 and 136 respectively positioned in openings 137 and 138 in the receiver housing 131. The movable jaw 140 carries a housing 141 for holding the U-shaped staples 142. Mounted behind this housing is a first pusher means 143 having fingers 144 which engage the back end or the span of the U-shaped staples. Second drive means 147 mounted at the rear of the jaw moves forwardly to drive the first drive means and push the staples out of the housing so that the legs of the staples engage the receiver. Along therewith pins 142 and 148 of the second drive means engage the pins 135 and 136 and push the pins through the opening in the housing into the receiving housing opening to push the pins 135 and 136 out of frictional engagement with the receivers thus allowing the receivers to interlock with the legs of the staple.

Figure 11:
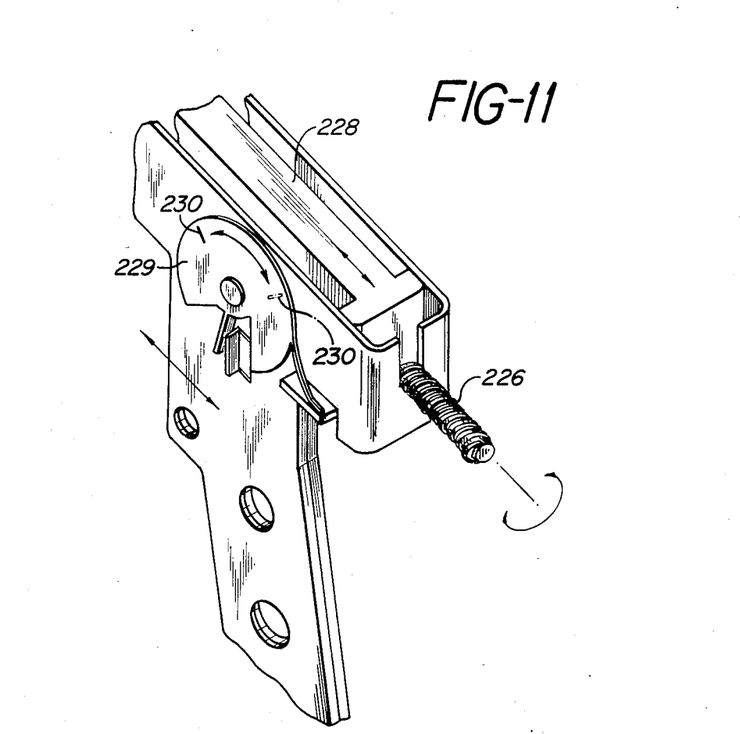
FIG. 11 is a perspective view of the inside of a portion of an instrument of the present invention depicting a gauge means for identifying the gap setting.

FIG. 11 is an enlarged cross-sectional view of a staple holding portion of a movable jaw 170 and a receiver holding portion of a stationary jaw 171 showing a receiver 172 in place in the stationary jaw. A staple 173 is in place in the movable jaw and the individual finger 174 driving means 174 for driving that staple is shown. The positioning of the jaws has been somewhat moved apart for the sake of clarity. In actual use, the tissue 175 is not rigid but is rather comformable and would tend to fill up the entire gap between the jaws.

Figure 12:
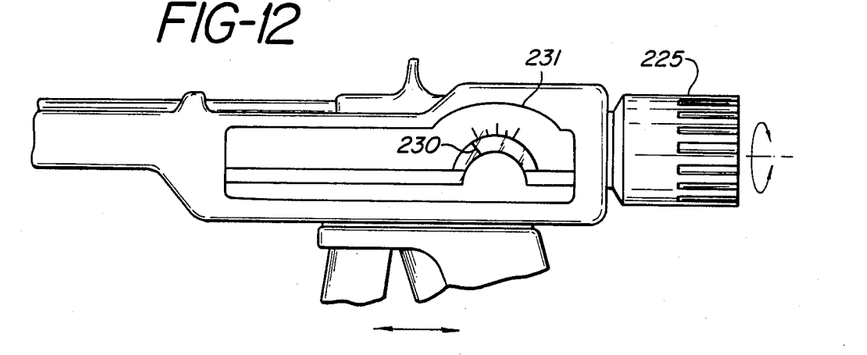
FIG. 12 is a side view of a portion of an instrument of the present invention showing the gauge for measuring the gap that has been set.

FIG. 12 is a cross-sectional view taken along Line 12—12 of FIG. 11. As may be seen each staple is held in position by movable flaps 176 disposed in the staple holding portion of the movable jaw.

Once the tissue has been clamped between the jaws and the jaws have been interlocked and aligned and made rigid, then the gap may be set between the jaws. It is important the operating surgeon know when he has attained the appropriate gap between the jaws. In many procedures, the surgeon will be unable to see the gap during the procedure as the business end of the instrument may be deep within the surgical cavity and unobservable to the operating surgeon. Hence, in preferred embodiments of the instruments of the present invention, there is a gauge adjacent the gap setting knob. One type of gauge that is preferred with the instruments of the present invention is depicted in FIGS. 11 and 12. As the control knob 225 is turned, the screw 226 moves forward. As the desired gap of 1.2 to 1.6 milimeters is reached the pusher 228 engages a rotatable member 229. The rotatable member has a mark 230 on it. Mounted on the outside of the housing is an appropriate gauge 231. As the gap comes to the correct setting the mark on the rotatable member becomes visible within the gauge on the outside of the instrument and the surgeon can see what gap is being set.

As may be appreciated the instruments of the present invention may be made from metals, plastics, woods, similar materials or various combinations thereof. If it is desired to make the instruments disposable, then the more inexpensive materials should be used. In most instances, it is desirable to make the instruments disposable because they are relatively complicated intricate mechanisms which are difficult to resterilize.

The general operation of the instruments of the present invention is as follows. The tissues to be joined are placed between the stationary jaw and the movable jaw and are clamped in the space therebetween by moving the tissue locking member in the direction of the stationary jaw to interlock therewith. The tissue locking members aligns the jaws and once engaged allows the gap setting knob to be turned. On turning the gap setting knob the staple housing with the staples and the pusher and drive means is moved towards the stationary jaw. An appropriate gap generally corresponding to the thickness of the tissues to be joined, is formed between the pair of jaws and is shown on the gauge. Thereafter, the interlock on the trigger mechanism is moved out of the way and the movable handle of the trigger mechanism actuated. This action forces the head of the pusher through the staple housing forcing the staples out of their holder through the tissue so that the legs pierce the tissue and engage the openings of the receivers held by the stationary jaw. Once the staple legs are engaged in the openings of the receivers, the friction holding means of the receivers is disengaged as well as the tissue locking member. After the joining operation has been completed, the gap between the jaws is opened by turning the gap control knob in the opposite direction.

It will be obvious to those skilled in the art that various modifications and changes may be made in the invention without departing from the spirit and scope thereof. The invention is not meant to be limited by that which is shown in the drawings and described in the specification. These changes and modifications are considered to fall within the scope of the present invention as defined by the appended claims.

What is claimed is:

1. A surgical instrument for stitching tissue by means of staples said instrument comprising: a support body, a pair of jaws mounted at one end of said support body, a staple housing mounted in one of said jaws, means mounted on said support body for moving said jaw containing said staple housing towards the other jaw to close the gap and clamp tissue placed therebetween, drive means mounted on said support body for driving the staples from the jaw on which the staple housing is mounted towards the opposite jaw, actuating means mounted at the end of said support body opposite said end on which the jaws are mounted for actuating said staple drive means, said actuating means comprising a stationary grip portion and a movable trigger portion, and means for preventing the actuation of said movable trigger portion until an appropriate gap is set between the jaws, said preventing means comprising a first pivotal lever mounted on said movable trigger portion, a second pivotal lever mounted on said stationary grip portion, said levers interlocking with each other to prevent movement of said movable trigger portion and means mounted on said support body for automatically pivoting said first pivotal lever out of interlocking relationship with said second pivotal lever when an appropriate gap has been set between the jaws of the instrument.

2. A surgical instrument according to claim 1 wherein the movable trigger portion is hollow and the first pivotal lever is mounted inside the hollow movable trigger portion and said first pivotal lever includes a clog extending through an opening in said hollow movable trigger portion and engaging said second pivotal lever to interlock therewith.

3. A surgical instrument according to claim 1 wherein the means for moving the first pivotal lever out of interlocking relationship comprises an ear disposed on the support body of the instrument which ear engages the first pivotal lever to pivot said lever out of interlocking relationship with said second pivotal lever.

* * * * *